United States Patent
Kaczperski et al.

(10) Patent No.: US 8,801,751 B2
(45) Date of Patent: Aug. 12, 2014

(54) NASAL SPLINT

(71) Applicants: Jeffrey Thomas Kaczperski, China Township, MI (US); Michael P. Pavlica, Chesterfield, MI (US); Vishal Banthia, San Jose, CA (US); Michael McDaniels, Rialto, CA (US); Lily Ayodele Roberts, San Francisco, CA (US); ZiHan Lin, Irvine, CA (US)

(72) Inventors: Jeffrey Thomas Kaczperski, China Township, MI (US); Michael P. Pavlica, Chesterfield, MI (US); Vishal Banthia, San Jose, CA (US); Michael McDaniels, Rialto, CA (US); Lily Ayodele Roberts, San Francisco, CA (US); ZiHan Lin, Irvine, CA (US)

(73) Assignee: Heal Medical LLC, Los Angeles, CA (US)

( * ) Notice: Subject to any disclaimer, the term of this patent is extended or adjusted under 35 U.S.C. 154(b) by 161 days.

(21) Appl. No.: 13/661,231

(22) Filed: Oct. 26, 2012

(65) Prior Publication Data
US 2014/0121696 A1    May 1, 2014

(51) Int. Cl.
*A61F 5/08*    (2006.01)

(52) U.S. Cl.
USPC .................................................. 606/204.45

(58) Field of Classification Search
USPC ........ 606/54, 55, 199, 204.45, 280, 283, 284, 606/285, 286, 298, 299; 602/5, 6, 17; 128/857, 858
See application file for complete search history.

(56) References Cited

U.S. PATENT DOCUMENTS

| | | | | |
|---|---|---|---|---|
| 2,398,073 A * | 4/1946 | Bonde | | 602/17 |
| 3,835,848 A * | 9/1974 | Berner | | 606/204.45 |
| 4,213,452 A | 7/1980 | Shippert | | |
| 4,274,402 A | 6/1981 | Shippert | | |
| 4,402,314 A | 9/1983 | Goode | | |
| 4,774,935 A * | 10/1988 | Aronsohn | | 606/204.45 |
| 5,022,389 A | 6/1991 | Brennan | | |
| 5,284,469 A * | 2/1994 | Jasen et al. | | 602/17 |
| 5,350,396 A | 9/1994 | Eliachar | | |
| 5,383,891 A * | 1/1995 | Walker | | 606/196 |
| 5,735,272 A * | 4/1998 | Dillon et al. | | 128/207.18 |
| 5,817,039 A | 10/1998 | Raunig | | |
| 5,890,486 A * | 4/1999 | Mitra et al. | | 128/200.24 |
| 5,931,799 A | 8/1999 | Guastella et al. | | |
| 5,947,123 A | 9/1999 | Shippert | | |
| 5,961,537 A * | 10/1999 | Gould | | 606/204.45 |
| 5,983,898 A | 11/1999 | Doyle | | |
| 6,322,590 B1 * | 11/2001 | Sillers et al. | | 623/10 |
| 6,352,548 B1 * | 3/2002 | Blach et al. | | 606/199 |
| 6,631,714 B2 * | 10/2003 | Von Duyke et al. | | 128/200.24 |
| 6,669,712 B1 * | 12/2003 | Cardoso | | 606/199 |

(Continued)

*Primary Examiner* — Jonathan W Miles
(74) *Attorney, Agent, or Firm* — Fitch, Even, Tabin & Flannery, LLP

(57) ABSTRACT

A nasal splint for effecting controlled support of the nasal pyramid, the splint, which can have a base portion of pyramid configuration, having a bridge portion and a pair of elongated wings on each side of the bridge portion extending laterally from the bridge portion thereof; an elastomeric device adjustably attachable on lateral edges of said wings to exert a force on said wings. The wings can also have at least one opening for fixedly positioning at least one compression head having a stud extending medially through the at least one opening. The base portion can be formed from a bendable frame laminated to a pliable membrane pad, the foam pad being disposed medially to the frame.

14 Claims, 15 Drawing Sheets

(56) References Cited

U.S. PATENT DOCUMENTS

| | | | |
|---|---|---|---|
| 6,823,864 B2 * | 11/2004 | Blach et al. | 128/200.24 |
| 7,000,611 B2 * | 2/2006 | Klemperer | 128/204.18 |
| 7,055,523 B1 * | 6/2006 | Brown | 128/206.11 |
| 7,105,008 B2 * | 9/2006 | Maryanka | 606/199 |
| 8,048,102 B2 * | 11/2011 | Thomas | 606/199 |
| 2003/0187374 A1 | 10/2003 | Nishioka | |
| 2007/0221219 A1 * | 9/2007 | Christy et al. | 128/203.16 |
| 2008/0082030 A1 | 4/2008 | Clark | |
| 2009/0234383 A1 * | 9/2009 | Ierulli | 606/204.45 |
| 2010/0042139 A1 * | 2/2010 | Honegger | 606/204.45 |
| 2010/0228282 A1 * | 9/2010 | Fenton | 606/204.45 |
| 2011/0106140 A1 * | 5/2011 | Obando | 606/204.45 |
| 2011/0270297 A1 * | 11/2011 | Judd | 606/199 |
| 2012/0010647 A1 * | 1/2012 | Pylyp | 606/199 |
| 2012/0022582 A1 * | 1/2012 | Guyuron et al. | 606/204.45 |

* cited by examiner

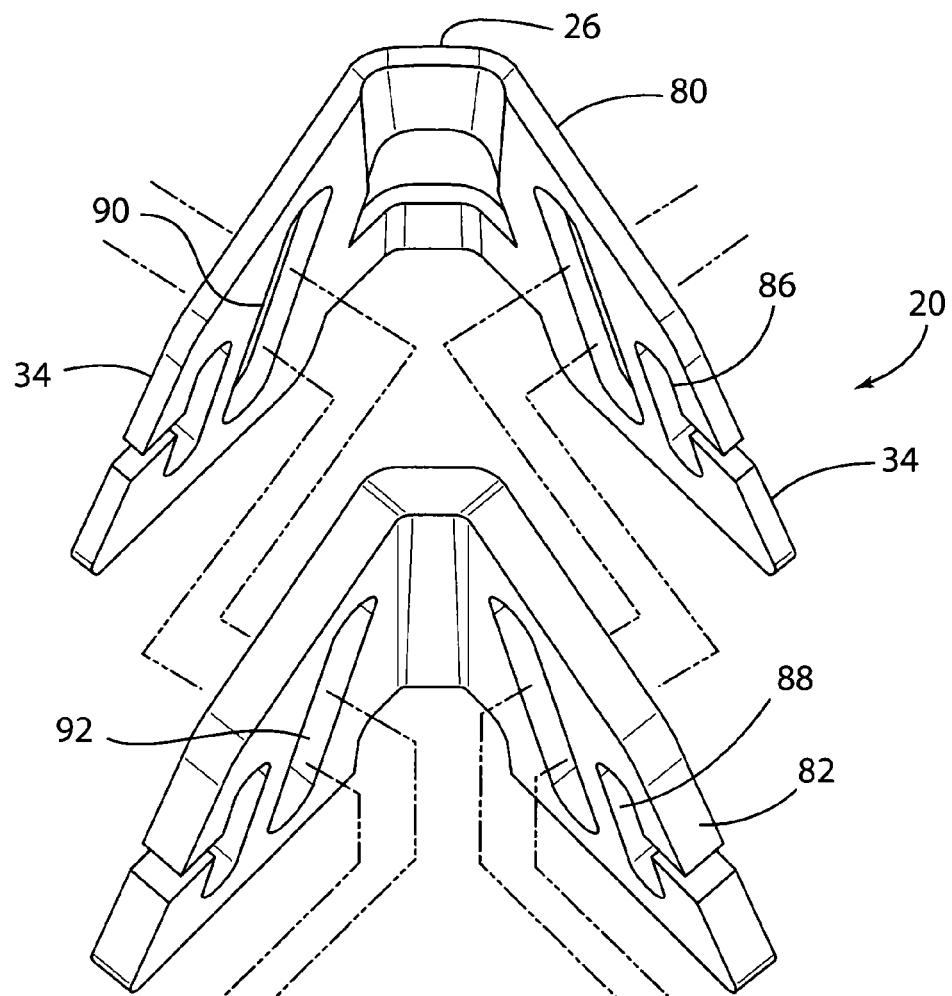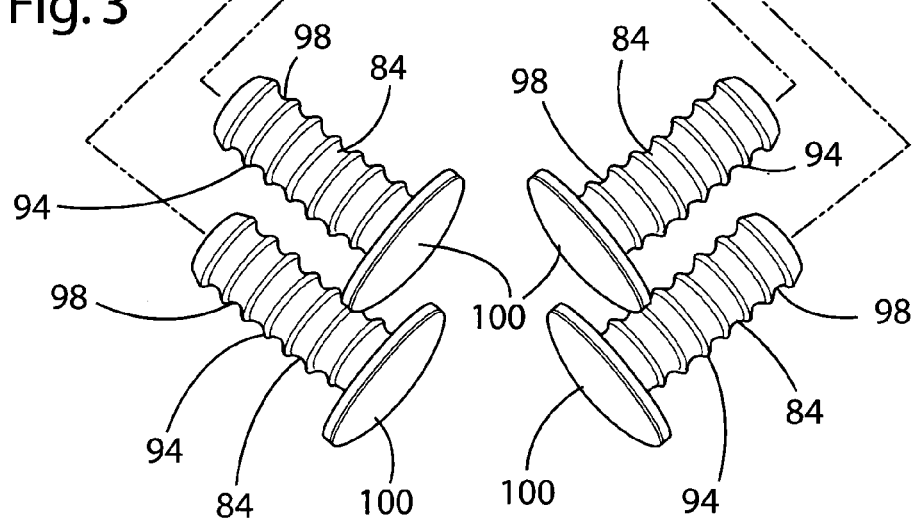
Fig. 3

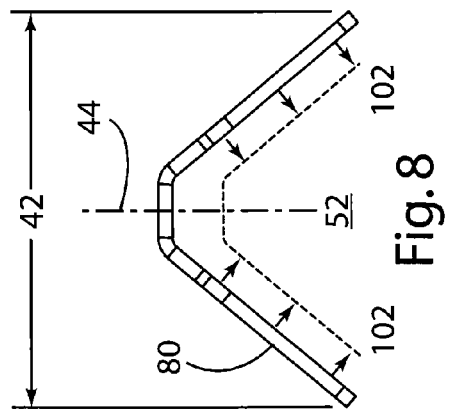
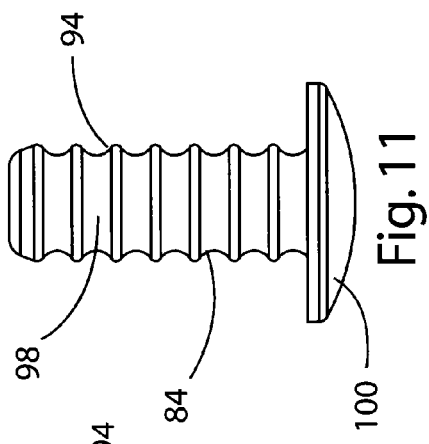
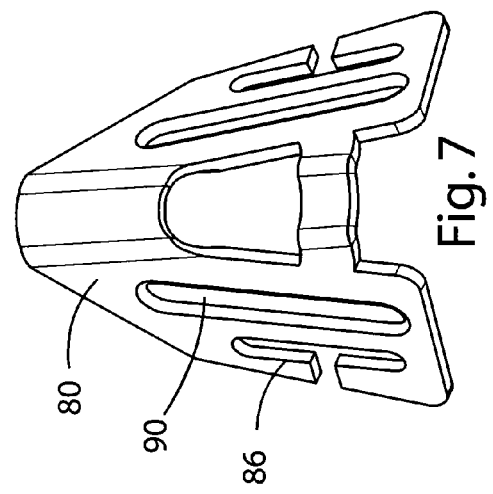
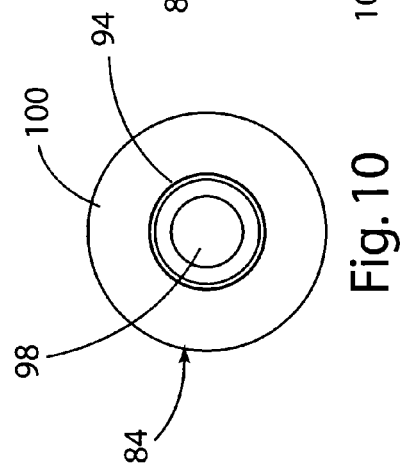
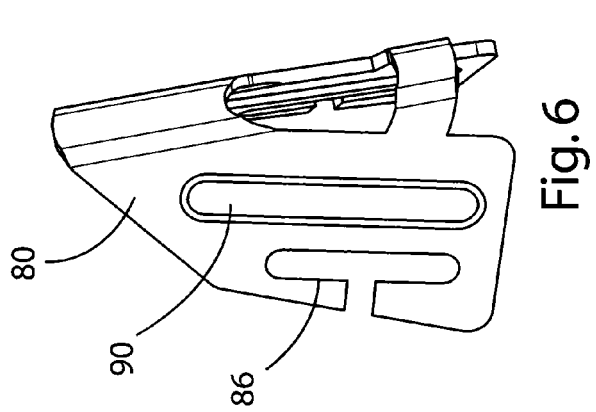
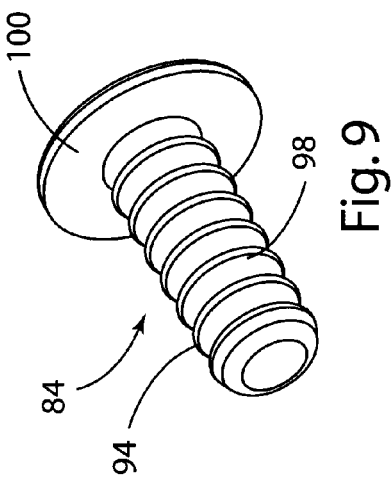

NASAL SPLINT

FIELD

The present products and methods relate to nasal splints, and in particular to nasal splint products, kits and methods that provide pressure points on the nasal pyramid of a human, which are selectable as to location and degree of compression.

BACKGROUND

Plastic surgery operations to the nose, i.e., rhinoplasty, are performed to treat nasal trauma, congenital nasal defects, cosmetic preferences, and the like. Rhinoplasty is the most frequently performed cosmetic surgical procedure in the United States. Most rhinoplasty and/or nasal reconstruction operations involve reshaping as well as strengthening a patient's nasal pyramid. A nasal pyramid includes both sides of the nose bridge at the nasal bone, upper lateral cartilage, and lower lateral cartilage sections.

Unfortunately, follow-up revision surgery is often necessary to correct post-operative nasal deviation after rhinoplasty. This is an obviously undesirable result due to the added emotional and physical trauma and added overall cost of the procedure. The post-operative deviation can result from repeated and unintended contact with the nose, such as sleeping postures that place biased forces on the nose, and the like. Deviation can also result from an inherent tendency for a nose to grow in the deviated direction.

One attempt to reduce post-operative nasal deviation is by applying a compressive force to the nasal pyramid. One compound splint sold under the trade name DENVER SPLINT by Shippert Enterprises, LTD of Centennial, Colo. provides a rigid base layer to follow the contour of the nose bridge. (See generally, U.S. Pat. No. 4,213,452 to Shippert). This type of splint provides little or no generalized compression, and is only used for about one week post-operatively as standard procedure. Also, rigid thermoplastic nasal splints, such as one sold under the trade name AQUAPLAST by Smith & Nephew Rolyan, Inc. of Menomonee Falls, Wis., can provide limited stabilization and protection to a nasal pyramid, post-rhinoplasty.

Despite these attempts in the art to improve rhinoplasty outcomes, further advances are possible and desirable.

SUMMARY

Accordingly, provided herein are embodiments that relate to nasal splints, and in particular to nasal splint products, kits and methods that provide pressure points on the nasal pyramid of a human, which are selectable as to location and degree of compression.

In one embodiment, an adjustable nasal splint kit provides a custom fit using adjustable pads disposed on a frame having a plurality of position points.

One embodiment provides a nasal splint for effecting controlled support of the nasal pyramid, the splint, which can have a base portion of pyramid configuration, having a bridge portion and a pair of elongated wings on each side of the bridge portion extending laterally from the bridge portion thereof; an elastomeric device adjustably attachable on lateral edges of said wings to exert a force on said wings. The wings can also have at least one opening for fixedly positioning at least one compression head having a stud extending medially through the at least one opening. The base portion can be formed from a bendable frame laminated to a pliable membrane pad, the foam pad being disposed medially to the frame. The bendable frame can be composed of a material selected from the list consisting of metals, titanium, rubber, carbon fibers, wood, plastic, elastomers, composites, combinations thereof, and the like. Optional features can include a cap to cover the compression head stud.

In some embodiments, the at least one opening for fixedly positioning at least one compression head can have a slotted opening on the base portion of each wing; and the at least one compression head being mountable at any point along the slotted opening and fixedly and extensively variable through the at least one opening. Also, in some embodiments, the slotted opening can be oriented on a longitudinal axis the base portion of the at least one wing. Also, the at least one compression head can be fixedly and extensively variable through the at least one opening by a plurality of frangible annular rings along a shaft of the compression head stud having a diameter greater than the opening. As an alternate embodiment, the at least one compression head can be fixedly and extensively variable through the at least one opening by a helical ridge along a shaft of the compression head stud having a diameter greater than the opening.

In some embodiments, the bridge portion can be flexible along a longitudinal axis to reduce a lateral dimension the base portion up to about 20 mm. Also, the elastomeric device, such as a headband, can provide a force on said wings to provide a force of up to 2 newtons on the at least one compression head.

In another approach, a nasal splint for effecting controlled support of the nasal pyramid can have a base portion of pyramid configuration, having a bridge portion and at least one elongated wing on at least one side of the bridge portion (26) extending laterally from the bridge portion thereof; an elastomeric device adjustably attachable on lateral edges of the at least one wing to exert a force on the at least one wing; the at least one wing further having at least one opening for fixedly positioning at least one compression head having a stud extending medially through the at least one opening. In one embodiment, the force of the compression head can be configured to provide up to 35 percent displacement of the patient's nasal tissue medially towards the patient's facial midline. The elastomeric device can be adjustable to provide simultaneous displacement of nasal tissue on both sides of a patient's face by at least one compression head. The nasal splint can be configured so that the volume, location and percentage of nasal tissue displacement can be adjustable by varying the number, position, and extension of stud head 100 with respect to device frame 20, and the force by the headband. A compressive force of the at least one compression head can be in the range of up to about 6 Newtons.

Other features will become more apparent to persons having ordinary skill in the art to which the package pertains and from the following description and claims.

BRIEF DESCRIPTION OF THE DRAWINGS

The foregoing features, as well as other features, will become apparent with reference to the description and figures below, in which like numerals represent like elements, and in which:

FIG. 3 illustrates an exploded perspective rear view of an exemplary nasal splint of the present embodiments;

FIG. 6 illustrates a perspective side view of an exemplary frame for a nasal splint of the present embodiments;

FIG. 7 illustrates a perspective front view of an exemplary frame for a nasal splint of the present embodiments;

FIG. 8 illustrates a top view of an exemplary frame for a nasal splint of the present embodiments;

FIG. 9 illustrates a perspective view of an exemplary compression stud for a nasal splint of the present embodiments;

FIG. 10 illustrates a bottom view of an exemplary compression stud for a nasal splint of the present embodiments;

FIG. 11 illustrates a side view of an exemplary compression stud for a nasal splint of the present embodiments;

DETAILED DESCRIPTION OF PREFERRED EMBODIMENTS

Figure 1:
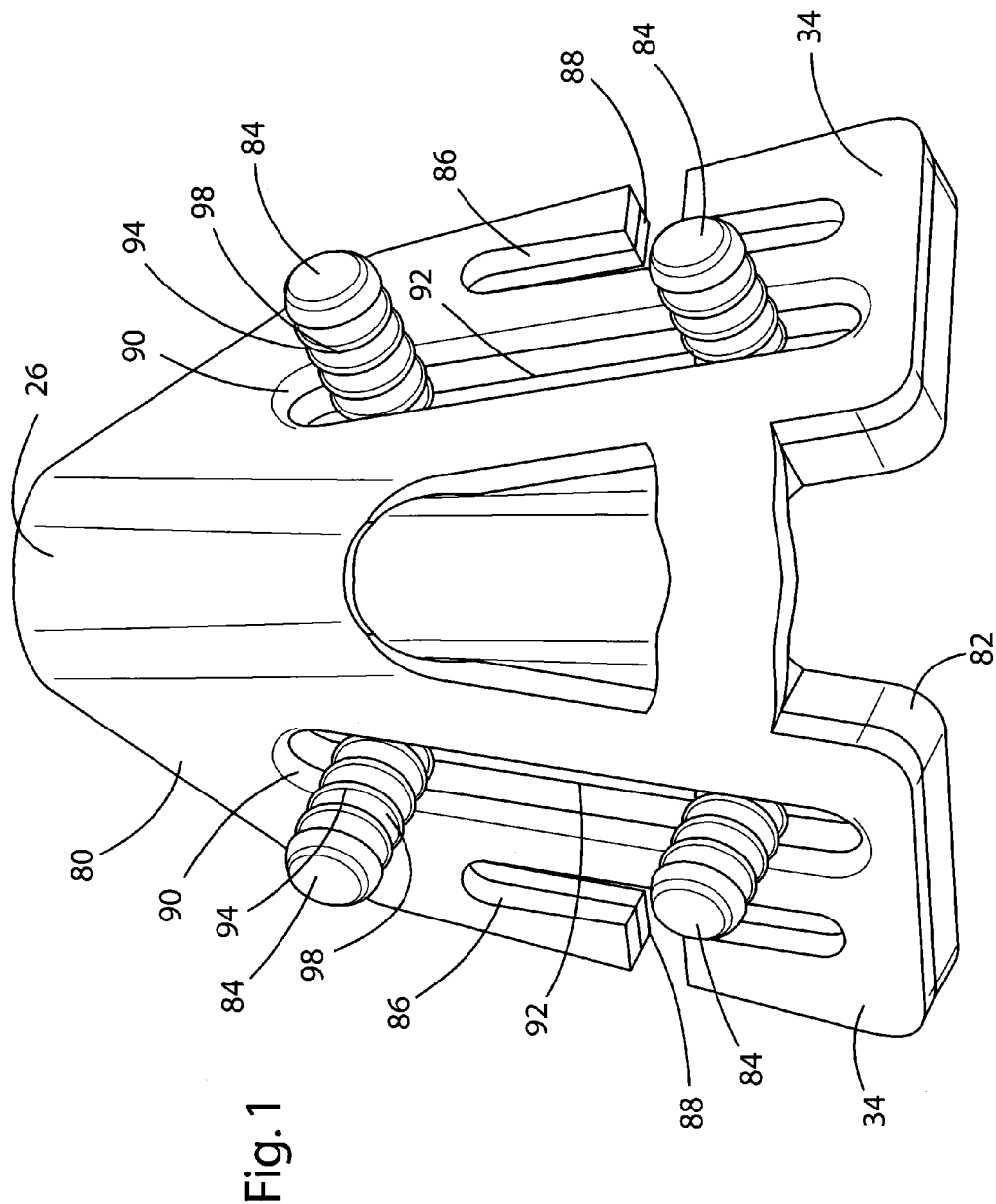
FIG. 1 illustrates a perspective front view of an exemplary nasal splint of the present embodiments.

Provided herein are embodiments that relate to nasal splints, and in particular to nasal splint products, kits and methods that provide at least one pressure point on the nasal pyramid of a human, which is variably positionable as to location and variable as to degree of compression. In use, the present embodiments can be configured to improve rhinoplasty and/or nasal reconstruction outcomes by reducing post-operative nasal deviation which can occur as nasal bones and tissues heal. The term 'rhinoplasty' is used herein to describe nasal surgical procedures. It is noted though that all the nasal surgeries, such as nasal reconstruction and the like, are included with the use of that term.

A physician can prescribe a customized compression configuration schedule using the present embodiments. For example, to aid in the understanding of how the present embodiments can be used, a multi-part schedule can be developed for each post-operative patient. Initially, this could include the present embodiments configured to provide a slightly progressive compression configuration to evaluate whether cartilage, bones, and the nasal pyramid/framework area are recovering correctly. Thereafter, a custom and more moderate nose-stabilizing method can be applied using the present nasal splint embodiment. This phase could last for several weeks and even up to one year. The physician/surgeon can evaluate and subsequently adjust the position and degree of compressive forces on the nose during follow-up appointments to minimize undesired deviation.

Generally, the present splint embodiments can provide a deformable/moldable frame to accommodate varying nasal profiles, while providing adjustable compressive forces to predetermined areas of a healing post-rhinoplastic nose. The magnitude and location of the compressive forces along the nasal profile can be adjusted as prescribed. Based on the knowledge of the procedure and the underlying nasal structure, the surgeon can apply a force such that the desired nasal deformation is achieved. Embodiments can include a frame that covers both sides of the nasal pyramid, though some embodiments cover only one side of the nasal pyramid.

The present splint, as described, would not require the use of an adhesive on the surface that contacts the skin, though use of an adhesive would not be prohibited either. In one approach, an adhesive could actually be used to provide a negative compressive force against the nasal pyramid (in other words the force on the skin is the reverse of the compressive force described herein using the pads and studs). In this instance, the adhesive could be applied only along the outer perimeter of the splint or internally at strategic locations (e.g., not on the screws/pads). The adhesive force would oppose the compressive force of to the screws/pads described herein; otherwise the splint will apply only uniform compression like DENVER splints.

The present nasal splint embodiments seek to address three preferable criteria of a customizable nasal splint, namely: to provide positionable compressive force, to provide variable intensity compressive force, and preferably to achieve these results without the use of an adhesive to the patient's skin. These criteria can be achieved using the nasal splint embodiments illustrated in the figures and the description below. Generally, as shown, the present nasal splints provide short-term and long-term treatments described above. Compressive inserts can be used immediately after surgery for more aggressive deviation prevention or treatment. And, more generalized pressure foam can be used for the remainder of the recovery period. Both compressive inserts and pressure foam can provide the desired adjustable compressive forces to the face.

Figure 5:
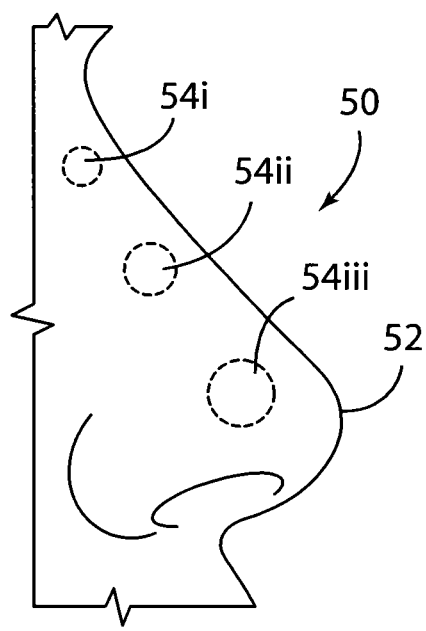
FIG. 5 illustrates exemplary points on a nose to selectively apply compression using nasal splint of the present embodiments.
Figure 13:
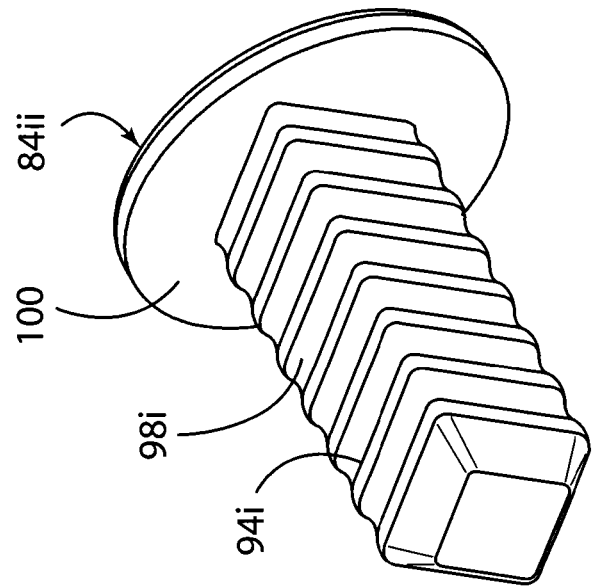
FIG. 13 illustrates a perspective view of another alternate exemplary compression stud for a nasal splint of the present embodiments.

Turning now to the figures, there is shown in FIG. 5 a profile of a portion of a human face generally indicated at 50. A nose 52 can have a multitude of areas 54, where forces can be selectively applied to maintain an optimal shape of the nose as set by the physician/surgeon during the nasal surgery. It is noted that areas 54 are provided for ease of understanding the present embodiments and it is understood that there are infinite other areas of the nose can be selected to provide compressive forces and still be within the scope of the present nasal splint and kits. Further it is noted that the present embodiments can apply force to either or both sides of nose 52.

Figure 4:
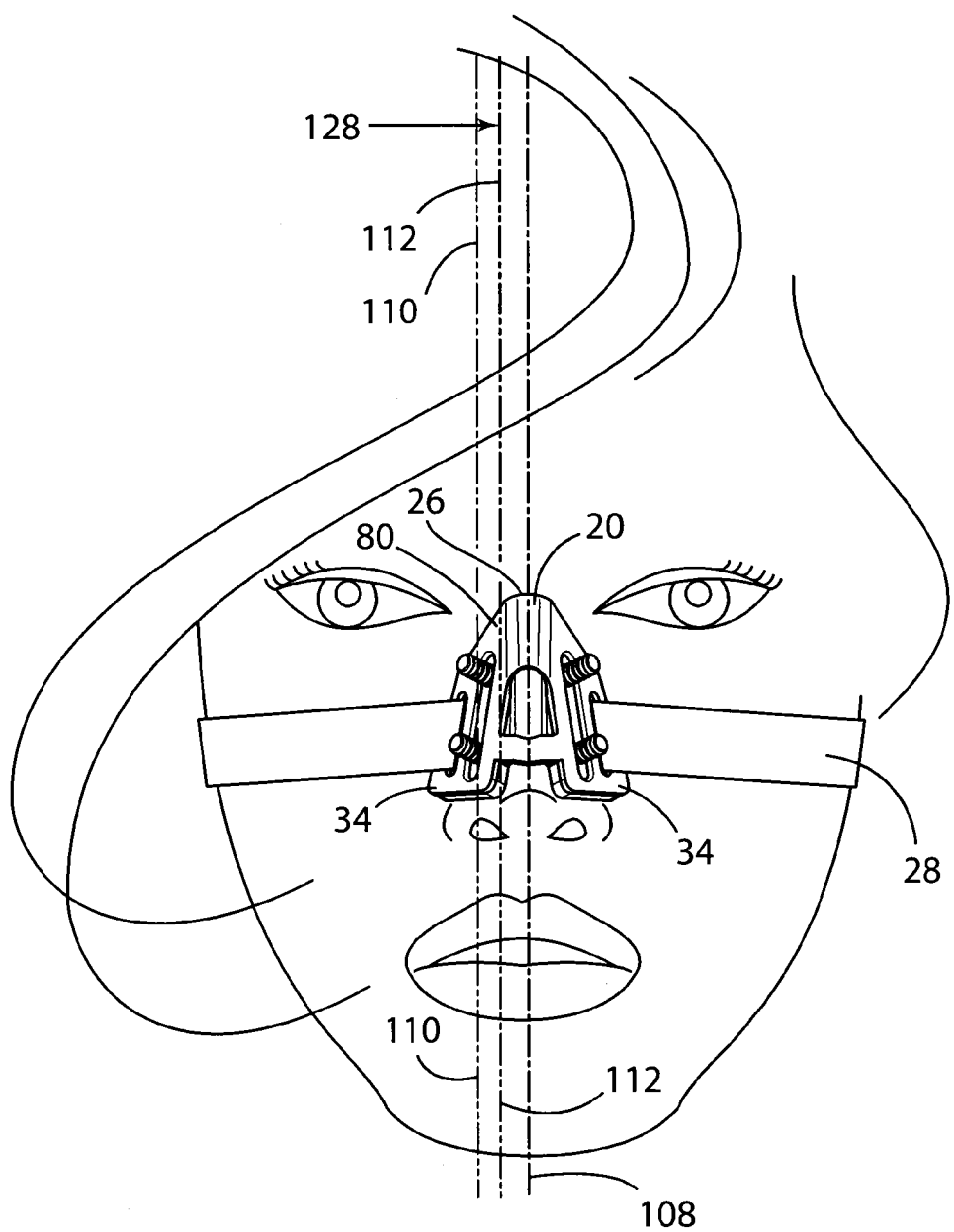
FIG. 4 illustrates a perspective plan view of an exemplary nasal splint of the present embodiments in use.

An exemplary splint of the present embodiments is shown in use generally at 20 in FIG. 4. As shown, splint 20 is attached by a headband 28. Head/neck band 28 can be positioned either above or below the patient's ears (not shown), though preferably below their ears. The general components of this embodiment can include a frame 80. Frame 80 can be made from of metals, titanium, rubber, carbon fibers, wood, plastic, elastomers, composites, combinations thereof, and the like. Frame 80 can be bendable or formable about a bridge portion/frame 26 and a pair of wing portions 34 to cover the patient's nasal pyramid.

Figure 20:
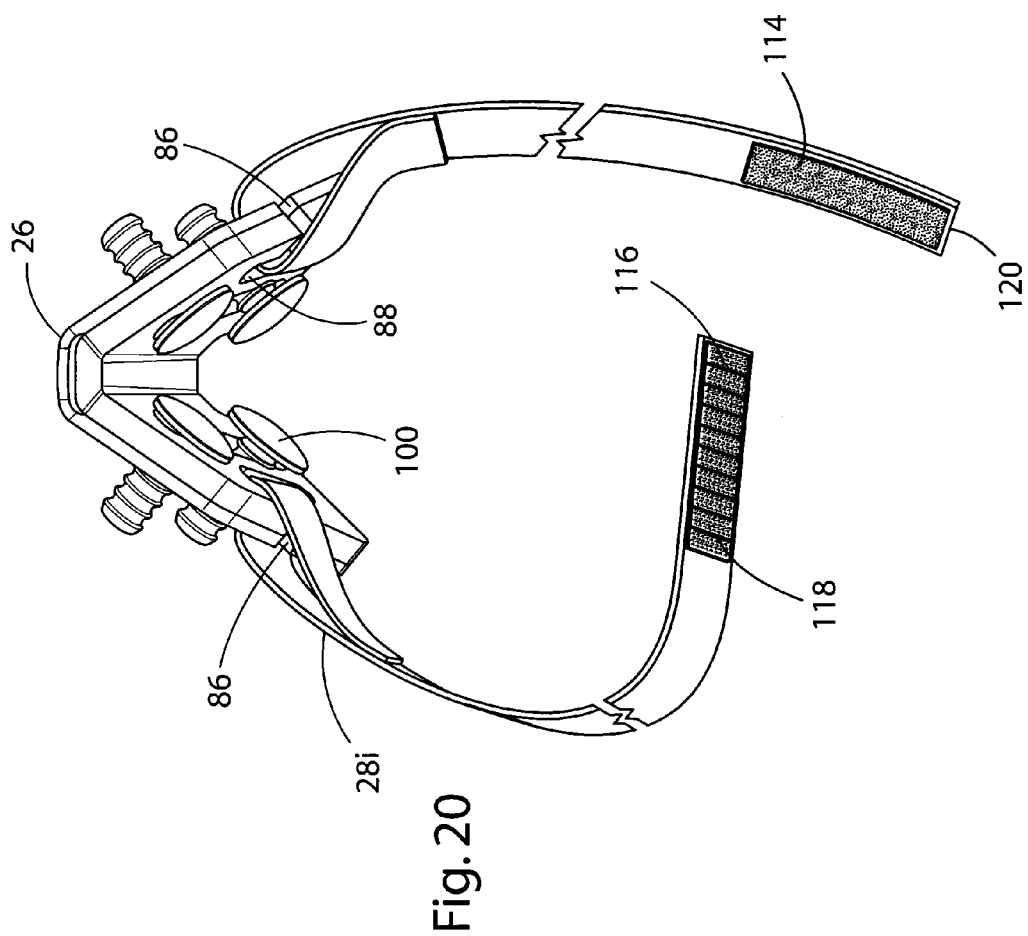
FIGS. 20-22 illustrate perspective views of exemplary headband alternatives of the present embodiments.
Figure 21:
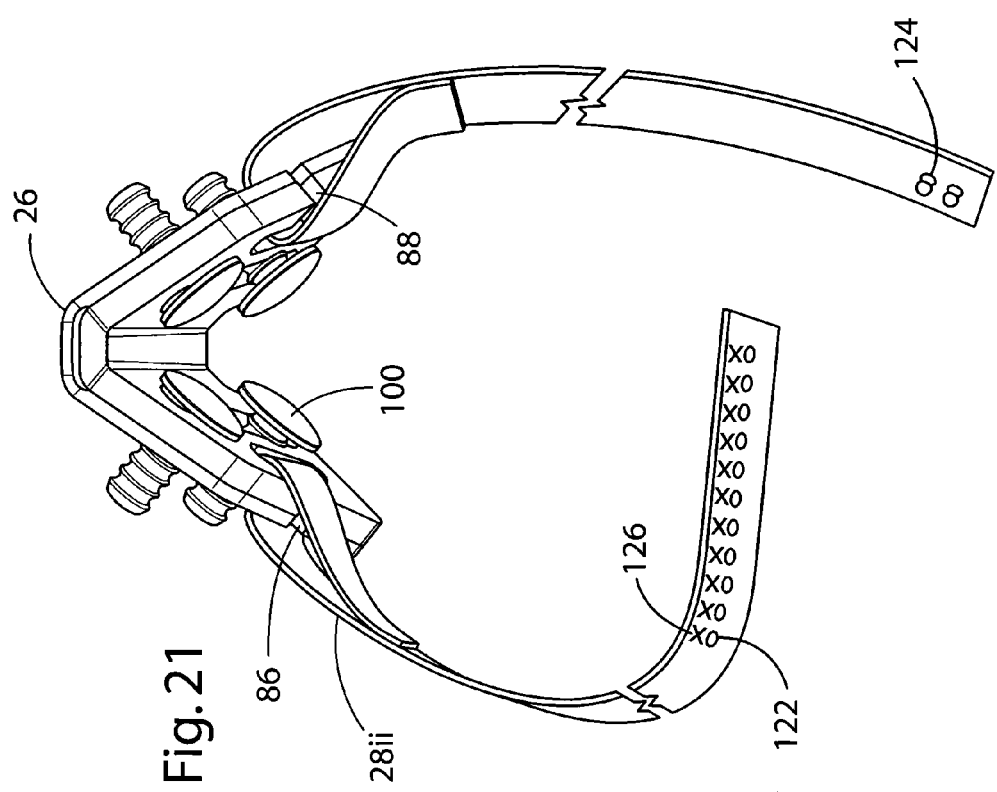

Headband 28 can be an elastic material and adjustable in length, and thus adjustable in the amount of compression by a hook and loop fastener, such as one sold under the trade name of VELCRO. For example, FIG. 20 illustrates a headband 28i shows a hooks 118 and loops 114 fastener to attached first and second ends of headband 28i. Position indicators 118 can be added to orient the patient as to the proper point of attachment of the first and second ends. Many other means of indicating desired attachment points of the headband 28 ends to the right tensioning position are possible within the scope of the present embodiments. As an alternate embodiment, FIG. 21 provides a headband 28ii having a first strap with a plurality of holes 122 to provide attachment by at least one corresponding peg 124 on a second strap of headband 28ii. In this embodiment, indicia 126 can be provided to assist a patient in orienting the fastening point of the two straps. Indicia can include letters, symbols, numbers, and the like.

Figure 22:
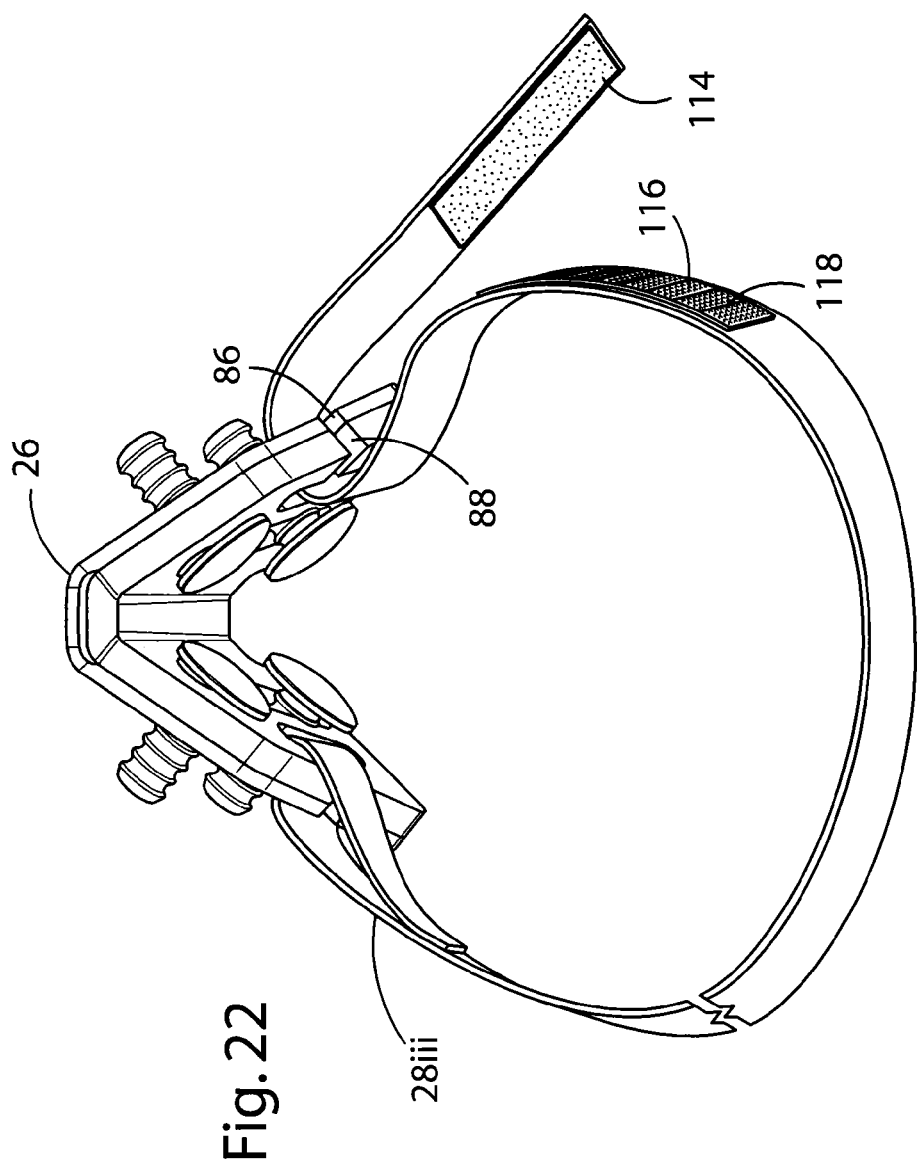

The headband 28 can have enough elasticity to allow a user to set the position of the closure point, and then place on their head. As shown, headband 28 can attach to frame 26 by looping through the openings found at frame cut-outs 86 and 88. Many other attachment configurations are possible within the scope of the present embodiments. Other headband embodiments can provide connections to the side and to the front including connection and adjustability at the frame 26 itself. For illustrative purposes, as shown in FIG. 22, headband 28iii attaches through the portion that loops through frame cut-outs 86 and 88.

Figure 2:
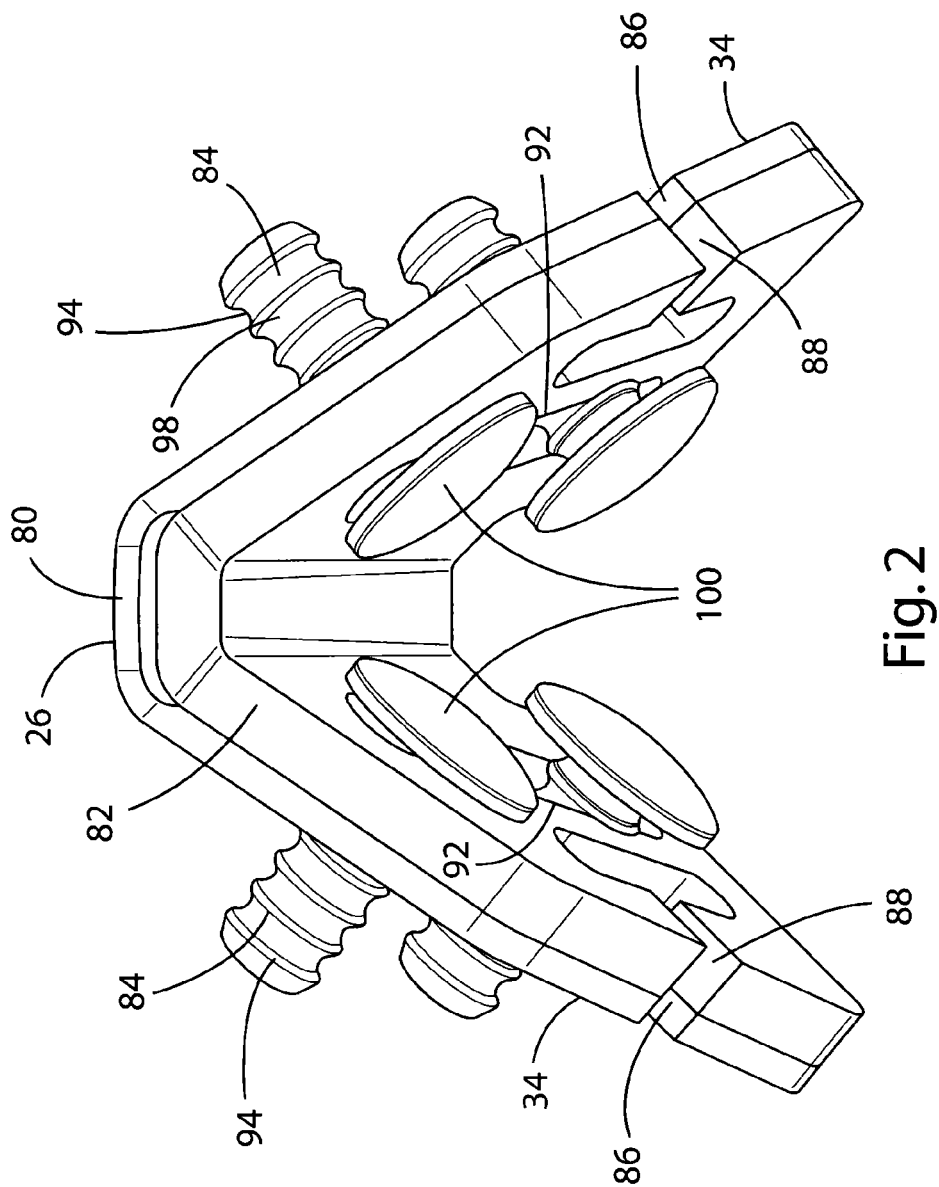
FIG. 2 illustrates a perspective rear view of an exemplary nasal splint of the present embodiments.

A more detailed view of an exemplary splint 20 embodiment is found in FIGS. 1-3. As shown, wing portions 34 of frame 80 can be laminated to a pliable pad 82 ("foam pad"). Foam pad 82 can be a closed cell or open cell foam laminated to the wing portion 34 by a bonding layer, such as a glue. Foam pad 82 and wing portions 34 have corresponding frame cut-out 86 and foam pad cut-out 88 for neck band attachment such as shown in FIG. 4. In the embodiment shown in FIGS. 1-3, a frame slot 90 is provided to slidably retain studs 84. As described herein, studs 84 can be extended and held at various positions along the length of its shaft 98. Stud shafts 98 extend through foam pad 82 by either a matching cutout, or as shown, as a foam pad slit 92. It is also noted that while the slots are illustrated in the longitudinal orientation of the frame, that other slot orientations (e.g., lateral, diagonal, combinations, and the like) are possible.

Figure 12:
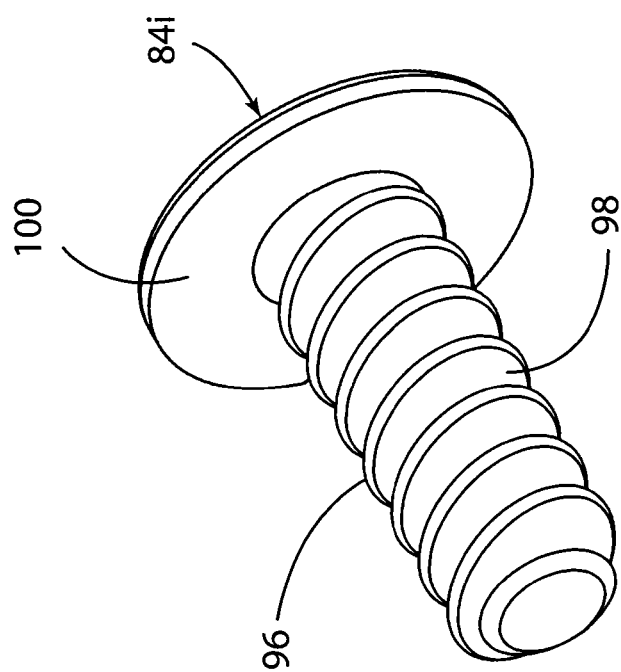
FIG. 12 illustrates a perspective view of an alternate exemplary compression stud for a nasal splint of the present embodiments.

The extension of stud shafts 98 can be retained through the use of annular rings 94 (FIGS. 1-3) or a helical screw (FIG. 12). As shown in FIG. 2, the stud shaft 98 terminates with a stud head 100. Stud head 100 provides the surface for the splint to apply compressive force (force) on a users nasal pyramid. FIGS. 9-13 shown additional exemplary stud configurations within the scope of the present embodiments. Studs 84 can be formed from a variety of flexible, resilient and/or deformable material. Exemplary materials can include plastics (such as an elastomer or thermal plastic), rubber, and the like. The material chosen should allow no more than about 20 percent of deformation as a result of the compressive force from headband 28.

FIGS. 6-8 show alternate views of frame 80. It is noted that in use, the neckband 28 can apply a force to reduce dimension 42 along the frame centerline 44. The reduction in dimension 42 is patient dependent, but the device may be able to be reduced in dimension by up to 20 mms of the overall lateral dimension of the base frame. It is noted that the embodiments could still function with little or even no reduction in dimension 42 so long as a compressive force (or pressure or tensioning) against a patient nasal tissue is provided as shown in FIG. 8 by direction arrows 102 is obtained against the patient's nose. The reduction in dimension 42 can be adjustable by the length and elasticity of headband 28. This force is adjustable as described above. The compressive force applied by each head 100 of stud 84 on a user can be in the range of up to about 6 N (newtons). In one embodiment, stud head 100 to be applied to the nasal tissue can be round (shown), oval, ovoid and the like and have a diameter in the range of about 2 to 20 mms in diameter of the surface to be applied to the nasal tissue, and preferably about 8 to 12 mms in diameter. The ratio of elastic force and compression force can by in the range of up to about 1:1.

The amount of force applied by stud head 100 of stud 84 can be configured to be adjustable by varying the tension of headband 28 to apply a force sufficient to medially displace (or deform) the patient's nasal tissue(s) at rest up to 35 percent the distance to the patient's facial midline. For illustrative purposes, FIG. 4 shows a patient's facial midline 108. As tension is applied by headband 28, stud head 100 applies force in direction 128 (irrespective of the angle from which the force is applied by stud head 100 to the nasal tissue) to the patient's nasal tissue displacing it medially from position 110 (the position of the nasal tissue with no force applied) to a position 112 medially to facial midline 108. As stated, the present embodiments should be configured to allow adjustability of the headband to allow up to 35 percent displacement of the nasal tissue medially towards the patient's face line. This degree of displacement can occur simultaneously on both sides of a patient's face by at least one stud head 100. Alternately, the volume, location and degree of nasal tissue displacement (or displacements) can be adjusted by varying the number, position, and extension of stud head 100 from the device frame 20, in addition to the tension applied by the headband.

As shown in FIG. 3, a user can place any number of studs 84, but at least one stud, along the length of slot 90 (and slit 92). One the position along the slot is determined, the user can continue to push against the stud head 100 until the desired amount of the extension of the head 100 from the from 80 is achieved.

Figure 15:
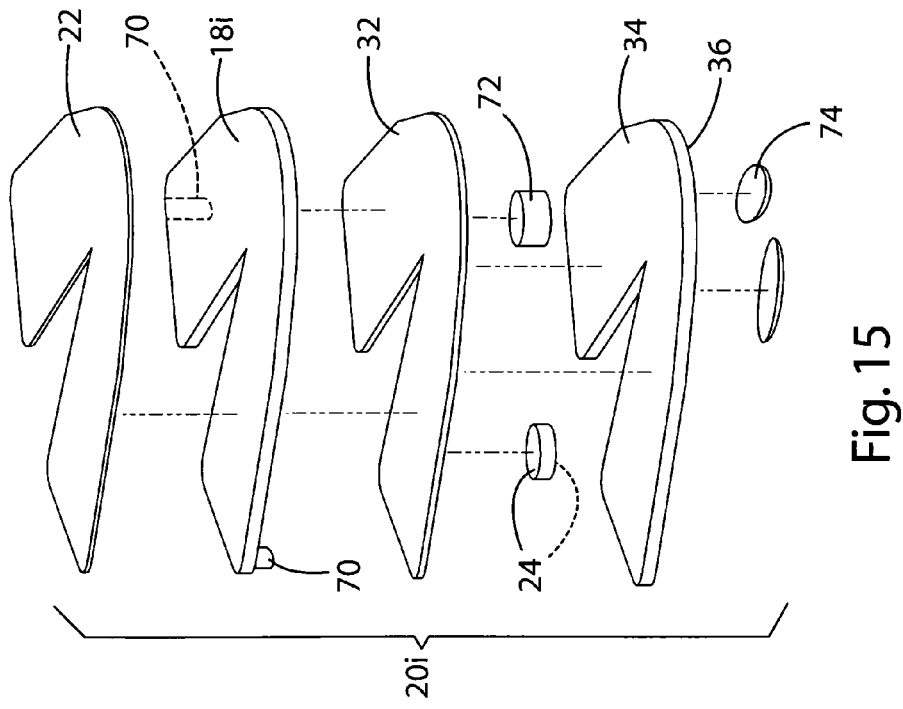
FIG. 15 illustrates an exploded perspective rear view of another exemplary nasal splint of the present embodiments.
Figure 14:
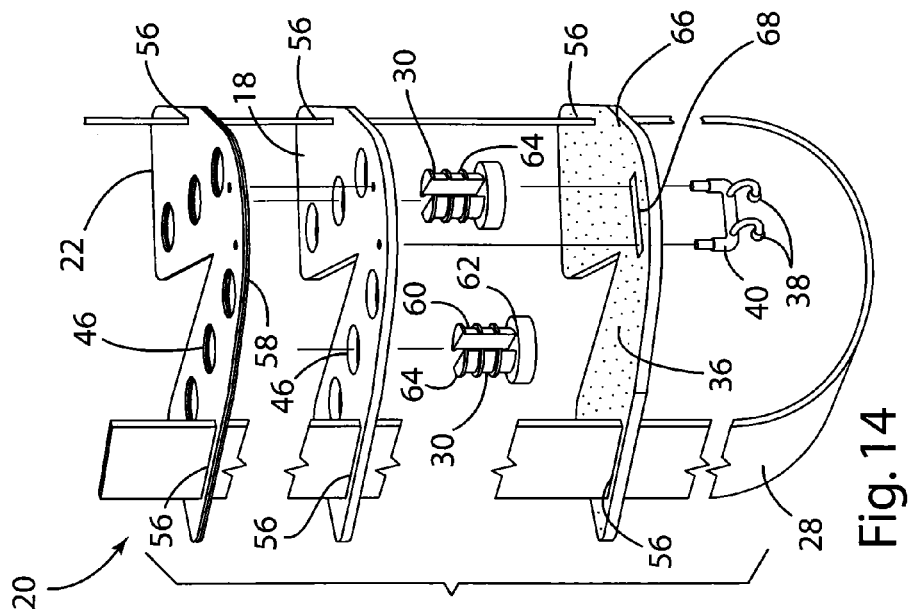
FIG. 14 illustrates an exploded perspective rear view of another exemplary nasal splint of the present embodiments.
Figure 16:
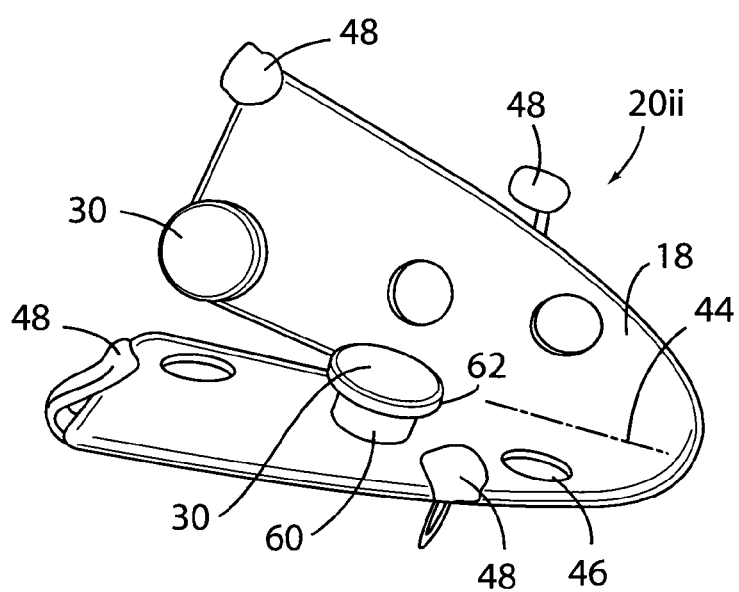
FIG. 16 illustrates a perspective rear view of another exemplary nasal splint of the present embodiments.

Other approaches are possible within the scope of the present splint 20 embodiments and are shown in FIGS. 14-16. In one approach shown in exploded view in FIG. 14, nasal splint generally indicated at 20 has compression inserts 30. As shown, nasal splint 20 has an exterior cover layer 22. Cover layer 22 can be configured to match the skin tone of the user or have other textures or patterning to provide an aesthetic to the splint and otherwise cover a rigid, but deformable, base frame 18. Cover layer 22 can be made from a variety of materials, such as one sold under the tradename LATEX adhesively attached to base frame 18 by placing an adhesive layer 58 on the side facing frame 18. It is noted though that cover layer 22 can be made from a other of materials, such as hypoallergenic materials. Frame 18 is preferably a malleable material, such as an aluminum stamping, that can be rigid yet capable of being shaped or formed to the configuration of the nose profile of a user. Preferably frame 18 is made from Aluminum 6061.

As illustrated, frame 18 (and frame cover 22) can have a plurality of openings 46 that are configured to correspond to desired pressure points 54 on a nose, such as those shown in FIG. 5. Openings 46 are designed to receive a shaft 60 having at least one compression insert 30 as desired by a health care provider. As with studs 94 above, inserts 30 can be of varying thickness and firmness formed injection molded plastic inserts (or liquid crystal polymer inserts) with a deformable/compressible shaft 60 (facing externally) and a compression head 62 directed inwardly toward the user. As shown, shaft 60 can even provide a vertical void to allow for easier insertion into opening 46. Preferably compression head 62 (like stud head 100) is flat and circular and preferably about 2 to 8 mm in diameter (range 2 mm to 18 mm) and preferably be about 2 mm to 3 (range 1 mm to 7 mm). Additionally, ribs/flanges as annular rings 64 can be added along the length of shaft 60 to provide variation of the extension of the insert 30 from frame 18. In use, shaft 60 can be pushed through a desired opening 46 to the desired distance.

Additionally, nasal splint 20 can have a skin contact foam layer 36. Foam layer 36 can preferably be made from a sheet of medical-grade foam with similar perimeter profile as frame 18 and covers head 62. A peelable adhesive layer 66 can be used to hold foam layer 36 to frame 18. Foam layer 36 can provide an interface that is comfortable for facial skin around the nose and diffuse the transmitted compressive force applied by inserts 30.

An elastic and/or adjustable headband 28 wrapped around the head/neck of a user can be used to provide the compressive force to the inserts 30. Headband 28 can optionally have a terry cloth covering and connect to the frame 18 via headband slots 56. Also, an optional nose clip 40 can be attached to frame 18 through nose clip slot 68. Nose clip 40 can be an injection molded part (or liquid crystal polymer part) and have nose pads 38 to gently pinch the nose bridge of a user. Nose clip 40 provides a means to fix and adjust the vertical position of nasal splint 20.

FIG. 15 provides another embodiment of an exemplary nasal splint 20. In this embodiment, nasal splint 20i has a frame cover 22 as described above attached to the base frame by an adhesive. A base frame 18i can be a custom-stamped, flexible aluminum structural frame of the device that can is malleable accommodate varying nasal profiles in different patients and can feature a pair of extensions 70 (preferably PTFE/parylene-coated extensions) positioned so that they can be bent inward at the entrance of a user's nostrils to hold the position of splint 18i in place. In alternate embodiments, a headband 28, such as shown in FIG. 4 can be used. Attached on frame 18 on the opposite side of the frame cover 22 is one side of a fastening means, such as a loop side 32 of a hook-and-loop fastener, such as one sold under the trade name VELCRO. The second side of the fastening means, such as the hook side 34 of a hook-and-loop fastener can be disposed beneath loop side 32 and be used to attach the skin contact foam layer bottom 36. It is noted though that in alternate embodiments fastening means 32 and 34 can be one adhesive layer and preferably a peelable adhesive layer.

Captured between fastening layers 32 and 34 can be pressure foam pads 72. Pads 72 can be dense circular foam shapes of varying thicknesses which can be adhered onto the Soft Velcro Layer—backside of Pressure Foam Pads to be Velcro (hook side)—or Foam Layer Bottom—backside of Pressure Foam Pads to be layered with adhesive. As with compression inserts 30, pads 72 can apply pressure on the nasal profile. The number, thickness, and density of pads 72 vary depending on the patient and are determined by the patient's health care provider. In this instance, pads 72 can be placed anywhere on the frame 18.

Additionally, optional nose pads 74 can be added internally on foam layer 36 to provide a stable resting point for the splint 20i and to maintain its vertical orientation. Nose Pads 74 can be made from a variety of materials, such as silicone molded oval structures much like those used on reading glasses.

In another approach shown in FIG. 16, a nasal splint is shown generally as 20ii. As illustrated, nasal splint 20ii is bent down a centerline 44 to accommodate the shape of a user's nose. Tabs 48 can be used to secure the frame to the patient with the tabs at the base used to extend into the patient's nostrils and the tabs at the top to pinch the nasal bone.

Figure 17:
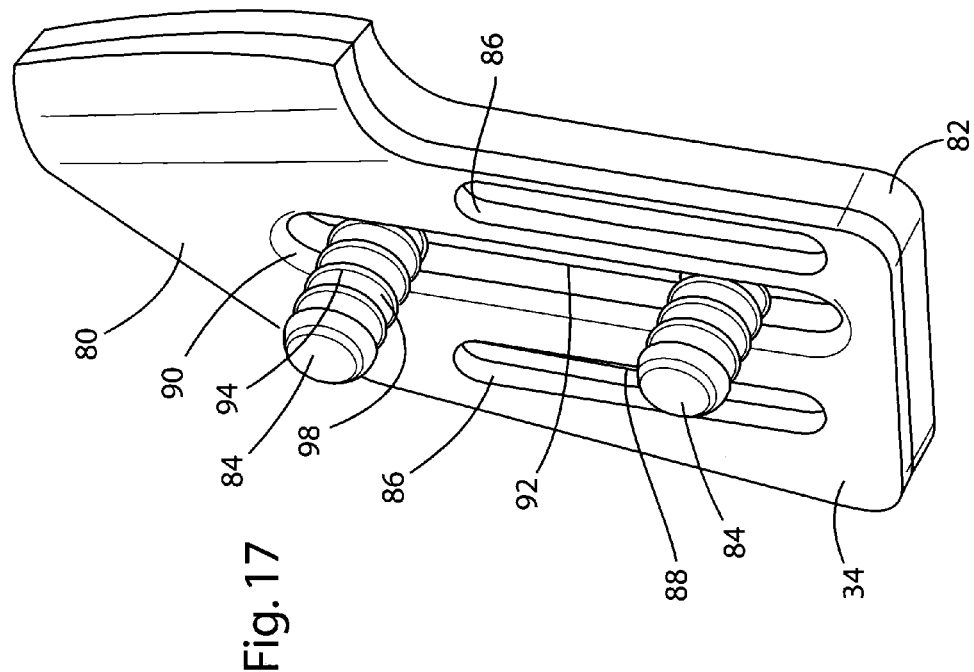
FIG. 17 illustrates a perspective front view of an exemplary nasal splint of the present embodiments according to another approach.

FIG. 17 illustrates a perspective front view of an exemplary nasal splint of the present embodiments according to another approach 20ii. In this approach, base frame 18ii only has one wing portion 34ii to apply to only one side of the nasal pyramid. It is noted that the base frame as illustrated is configured for the right-hand side of the nasal pyramid. A reciprocal left-hand base frame (not shown) can also be applied in applications needing compressive force on the left-hand side of the nasal pyramid.

Figure 18:
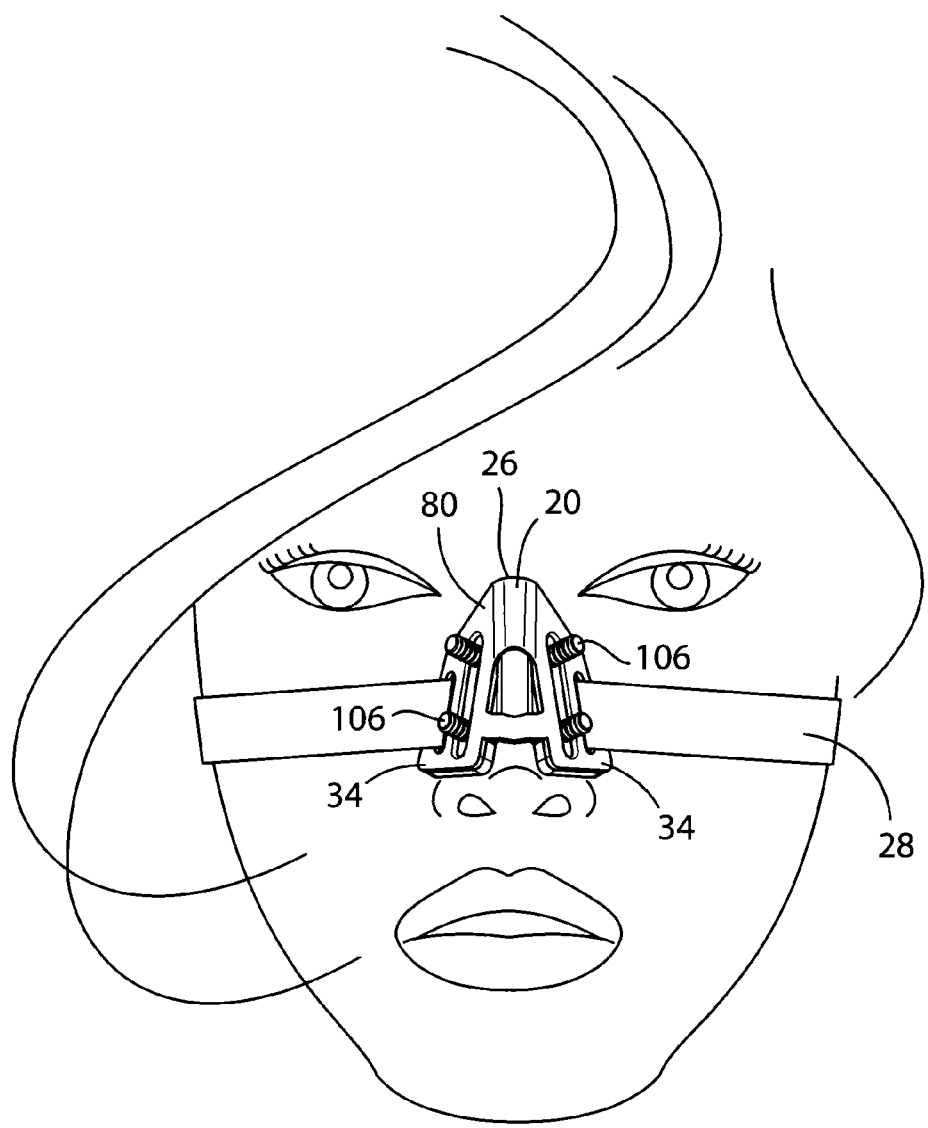
FIG. 18 illustrates a perspective front view of an exemplary nasal splint of the present having an optional stub cap.
Figure 19:
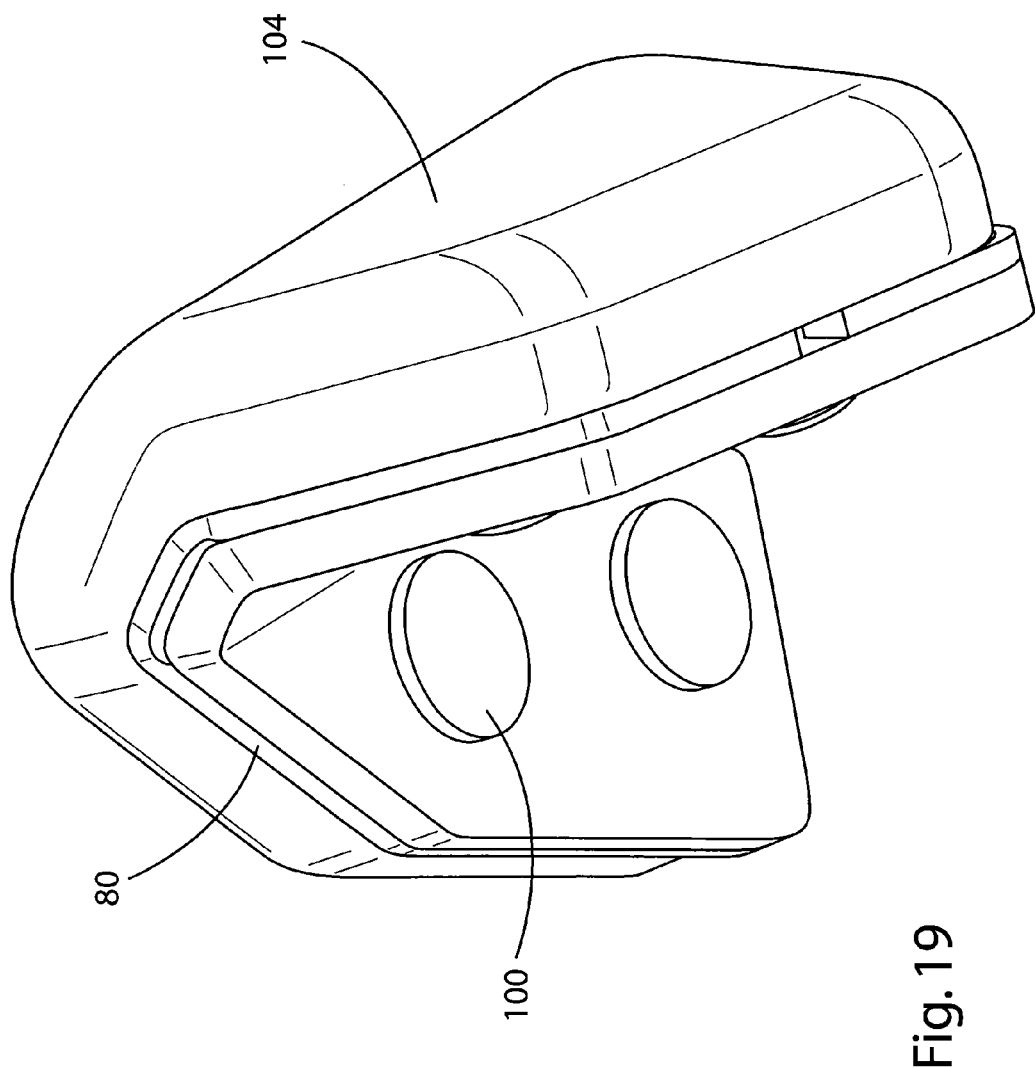
FIG. 19 illustrates a perspective front view of an exemplary nasal splint of the present having an optional frame cap.

FIG. 18 illustrates a perspective front view of an exemplary nasal splint of the present having an optional stub cap. As shown, cap 106 can cover the stud portion 84 of the compression head. FIG. 19 illustrates a perspective front view of an exemplary nasal splint of the present having an optional frame cap. In this instance, cap 104 covers the base frame 18. Cap 104 can be any type of thermoplastic, polypropylene, metal, rubber, wood, composite, and combinations thereof; and preferably a thermoplastic.

In use, nasal splint 20 can be configured and applied to a patient by a health care professional directly after a rhinoplasty procedure, and nasal splint 20i can be applied in the health care provider's office during a follow up visit. No additional or specialized equipment or tools are necessary for the physician to prepare the device. During preparation, the angle of the base frame can be formed to match the profile of the patient's nose. In addition, the position and degree of the compression inserts or pressure foam pads can be adjusted. The present design provides for fast and efficient configuration while providing customization than is currently known in the art.

A patient can wear nasal splint while at rest, e.g., sleeping. The patient is thus provided with, on average, between about 5 hours up to 24 hours of treatment daily. The assumption is that after daily treatment for up to about a year, the patient's nasal profile should remain as straight as the rhinoplasty procedure had intended it to be. Additionally, since the patient can use the splints in a home setting, the level of emotional trauma and discomfort can be reduced because he or she does not have to wear the device during all parts of their daily life. Adjustable headbands can also be varied to increase the degree of compression.

Optional embodiments can also be included in the present nasal splint configuration to provide even further levels of customization. The health care provider may be able to calculate the configuration of the nasal splint and have a device to produce a custom non-adjustable piece.

Although the present embodiments use an adjustable headband and inserts, there are many ways to offer external compressive forces. For example, some embodiments can provide external compression by other types of fluid and/or mechanical means. External compression can include viscous injection, adjustable air/fluid bladders (which can be compartmentalized into a plurality of bladders) with injection ports, stretchable pouches, leveling screws, tightening screws, spring-screws, collapsible screws, 90° tube opening, buckling domes, and nitinol-mesh skeletons.

While preferred embodiments have been described in detail, variations and modifications can be effected within the scope of the present embodiments.

We claim:
1. A nasal splint for effecting controlled support of the nasal pyramid, the splint comprising:
    a base portion of pyramid configuration, having a bridge portion and a pair of elongated wings on each side of the bridge portion extending laterally from the bridge portion thereof;

an elastomeric device adjustably attachable on lateral edges of said wings to exert a force on said wings;

at least one compression head having a stud, the stud attachable to said wings; and the wings further comprising at least one opening for fixedly positioning the attachable stud, the stud extending medially through the at least one opening;

wherein the at least one opening is a slot on each wing of the base portion;

wherein the at least one compression head is fixedly attachable anywhere along a length of the slot.

2. The nasal splint of claim 1, wherein the base portion comprises a bendable frame laminated to a pliable membrane pad, the pliable membrane pad being disposed medially to the frame.

3. The nasal splint of claim 2, wherein the bendable frame is composed of a material selected from the list consisting of metals, titanium, rubber, carbon fibers, wood, plastic, elastomers, composites, and combinations thereof.

4. The nasal splint of claim 1, further comprising a cap to cover the at least one compression head stud.

5. The nasal splint of claim 1, wherein the slot is oriented on a longitudinal axis the base portion of the at least one wing.

6. The nasal splint of claim 1, wherein the at least one compression head is fixedly and extensively variable through the at least one opening by a plurality of frangible annular rings along a shaft of the compression head stud, the shaft having a diameter greater than the at least one opening.

7. The nasal splint of claim 1, wherein the at least one compression head is fixedly and extensively variable through the at least one opening by a helical ridge along a shaft of the compression head stud, the helical ridge having a diameter greater than the at least one opening.

8. The nasal bridge of claim 1, wherein the bridge portion is flexible along a longitudinal axis to reduce a lateral dimension of the base portion up to about 20 mm.

9. The nasal bridge of claim 1, wherein the elastomeric device provides a force on said wings to provide a force of up to 2 newtons on the at least one compression head.

10. A nasal splint for effecting controlled support of the nasal pyramid, the splint comprising:

a base portion of pyramid configuration, having a bridge portion and at least one elongated wing on at least one side of the bridge portion extending laterally from the bridge portion thereof;

an elastomeric device adjustably attachable on lateral edges of the at least one wing to exert a force on the at least one wing;

at least one compression head having a stud, the stud attachable to said at least one wing;

the at least one wing further comprising at least one opening for fixedly positioning the attachable stud, the stud extending medially through the at least one opening;

wherein the at least one opening is a slot on the at least one wing of the base portion;

wherein the at least one compression head is fixedly attachable anywhere along a length of the slot.

11. The nasal splint of claim 10, wherein the force of the at least one compression head is configured to provide up to 35 percent displacement of nasal tissue medially towards a facial midline.

12. The nasal splint of claim 11, wherein the elastomeric device is adjustable to provide simultaneous displacement of nasal tissue on both sides of a face by the at least one compression head.

13. The nasal splint of claim 10, wherein a volume, location and percentage of nasal tissue displacement is adjustable by varying a number, position, and extension of the at least one compression head with respect to the base portion, and the force by the elastomeric device.

14. The nasal splint of claim 10, wherein a compressive force of the at least one compression head is in the range of up to about 6 newtons.

\* \* \* \* \*